United States Patent [19]

Sage, Jr. et al.

[11] Patent Number: 5,302,172
[45] Date of Patent: Apr. 12, 1994

[54] METHOD AND COMPOSITION FOR IONTOPHORESIS

[75] Inventors: Burton H. Sage, Jr.; Jim E. Riviere, both of Raleigh, N.C.

[73] Assignees: North Carolina State University, N.C.; Becton Dickinson and Company, N.J.

[21] Appl. No.: 653,202

[22] Filed: Feb. 8, 1991

Related U.S. Application Data

[63] Continuation-in-part of Ser. No. 494,062, Mar. 15, 1990, abandoned.

[51] Int. Cl.$^5$ .............................................. A61N 1/30
[52] U.S. Cl. ......................................... 604/20; 604/49
[58] Field of Search ................... 604/20, 49; 128/798, 128/802, 803, 898

[56] References Cited

U.S. PATENT DOCUMENTS

| | | | |
|---|---|---|---|
| 3,991,755 | 9/1976 | Vernon et al. | 604/20 |
| 4,406,658 | 9/1983 | Lattin et al. | 604/20 |
| 4,702,732 | 10/1987 | Powers et al. | 604/20 |
| 4,752,285 | 6/1988 | Petelenz et al. | 604/20 |
| 4,820,263 | 4/1989 | Spevak et al. | 604/20 |
| 4,950,229 | 8/1990 | Sage, Jr. | 604/20 |
| 5,023,085 | 6/1991 | Francoeur et al. | 604/20 |
| 5,047,007 | 10/1990 | McNichols et al. | 604/20 |
| 5,057,072 | 10/1991 | Phipps | 604/20 |
| 5,068,226 | 11/1991 | Weinshenker et al. | 604/20 |
| 5,084,006 | 1/1992 | Lew et al. | 604/20 |
| 5,084,008 | 1/1992 | Phipps | 604/20 |
| 5,088,977 | 2/1992 | Sibalis | 604/20 |
| 5,135,480 | 8/1992 | Bannon et al. | 604/20 |

OTHER PUBLICATIONS

Lattin, Gary A. "Method to Control Delivery of Unchanged Drugs via Iontophoresis" JRE Nov. 1988.
D. I. Abramson, et al., *Arch Environ Health* 19:103 (1969).
D. I. Abramson, et al., *American Heart Journal* 23;817 (1942).
H. A. Kontos, et al., *Circulation Research* 21:679 (1967).
N. H. Bellantone, et al., *International Journal of Pharmaceutics* 30:63 (1986).

*Primary Examiner*—John D. Yasko
*Assistant Examiner*—Michael Rafa
*Attorney, Agent, or Firm*—Bell, Seltzer, Park & Gibson

[57] ABSTRACT

The invention discloses methods and compositions for enhanced iontophoretic delivery of active agents. The compositions are pharmaceutically acceptable compositions for iontophoretic delivery comprising a delivery enhancing amount of a vasodilator and active agent. Methods comprise adding a delivery enhancing amount of a vasodilator to an active agent and delivering by iontophoresis.

11 Claims, 3 Drawing Sheets

METHOD AND COMPOSITION FOR IONTOPHORESIS

CROSS REFERENCE TO RELATED APPLICATION

This application is a continuation in part of patent application Ser. No. 07/494,062, filed Mar. 15, 1990 abandoned.

FIELD OF THE INVENTION

The invention relates to iontophoretic transdermal delivery. More specifically, the invention relates to methods and compositions for enhancing iontophoretic delivery.

BACKGROUND

During iontophoresis, charged compounds pass from a reservoir attached to the skin of a person or animal into the tissue therebeneath. The process is one wherein the rate of delivery is a function of current, active agent concentration, and presence of other ions. It is a generally held belief that higher concentration of compound, higher levels of current, and lower concentration of other ions will result in greater delivery of the compound.

L. Brown and R. Langer, *Ann. Rev. Med.* 39:221 (1988) describe the generally held belief that the rate limiting barrier for transdermal drug delivery is the stratum corneum. There continues to be a large research effort to find methods to reduce or eliminate the rate limiting property of the stratum corneum.

N.H. Bellantone et al., *International Journal of Pharmaceutics* 30:63 (1986) describes how iontophoresis can be used in place of other means to enhance drug transport through the epidermal barrier such that the need for chemical penetration enhancers could be obviated. Alternatively, the article suggests use of penetration enhancers could lower drug concentrations or lower energy required for delivery.

Another technique believed to enhance the delivery of certain types of active agents by iontophoresis is disclosed in European patent application 0 278 473 A1. The application describes the addition of compounds to proteins and other macromolecules to decrease the degree of aggregation of the molecules in the active reservoir. The added compounds have the ability to aid solubility and disassociation of the macromolecules.

It is also well-known in the iontophoresis art (for example, see "Iontophoretic Delivery of Nonpeptide Drugs Formulation Optimum for Maximum Skin Permeability" by J. E. Sanderson et al, *J. Pharm Sci.* 78:361 (1989) that the presence of ions other than the desired compound in the donor reservoir formulation reduces iontophoretic efficiency.

In the situation of transdermal delivery where the rate limiting barrier is the stratum corneum, the dermal vasculature, which acts as the means of compound removal from the dermal tissue, has no effect on the delivery rate. Regardless of its state of dilation, it is capable of removing all the compound that reaches it. Otherwise, the vasculature would become the rate limiting barrier.

If the stratum corneum is the rate limiting barrier, placing a vasodilator near the dermal vasculature for the purpose of enhancing the blood flow through the dermal vasculature by any means, would have no effect. The rate of delivery would still be limited by the stratum corneum.

Vasodilators such as tolazoline, nitrates, papaverine, phentolamine, dipyridamole, cyclandelate, isoxsuprine, mecholyl (metacholine), histamine and nylidrin are known to dilate blood vessels. Their use with iontophoresis, without other agents, has been studied. Studies include, for example, D.I. Abramson et al., *American Heart Journal,* 23:817 (1942) which describes a significant increase in blood flow when using vasodilators alone.

Iontophoresis of vasodilators as a means of enhancing delivery of an active agent delivered with it has not been demonstrated. Despite attempts to optimize iontophoretic delivery by such means as varying compound concentrations and optimizing ionic moieties in the system, the efficiency of iontophoretic delivery is still low.

SUMMARY OF THE INVENTION

The invention discloses methods and compositions for enhanced iontophoretic delivery of active agents.

The compositions are pharmaceutically acceptable compositions for iontophoretic delivery which comprise a delivery enhancing amount of a vasodilator and active agent.

Other embodiments of the invention include methods for enhancing iontophoretic delivery of active agents which comprise adding a delivery enhancing amount of a vasodilator to an active agent and delivering by iontophoresis.

DETAILED DESCRIPTION OF THE INVENTION

Figure 1:
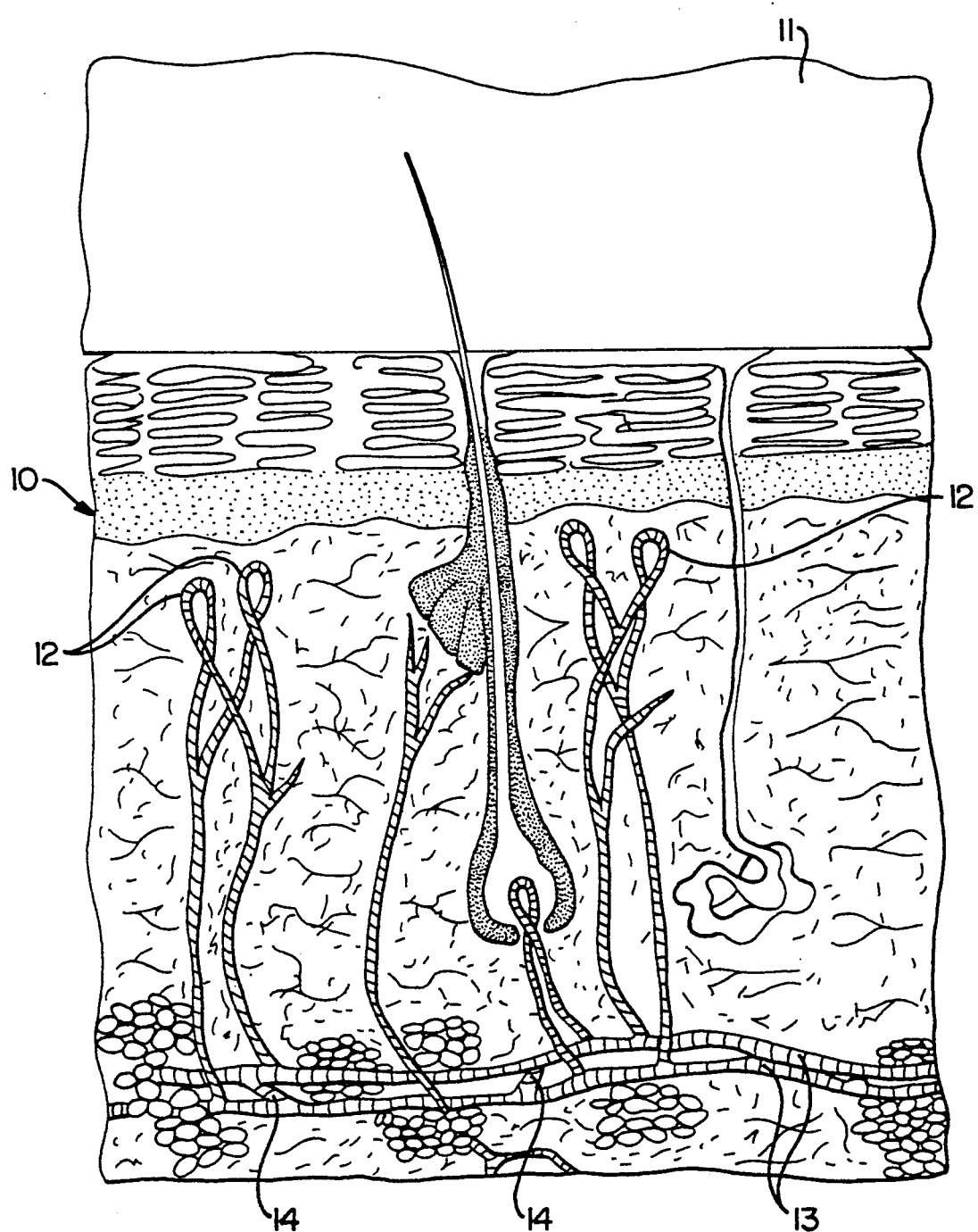
FIG. 1 is a schematic presentation of the skin (10), which shows the upper capillary loops (12) of the vasculature of the skin and the deeper blood vessels that feed the upper capillary loops and the shunt blood vessels (14) which connect the deeper blood vessels.

While this invention is satisfied by embodiments in many different forms, there is shown in the drawings and will herein be described in detail, preferred embodiments of the invention, with the understanding that the present disclosure is to be considered as exemplary of the principles of the invention and is not intended to limit the invention to the embodiments illustrated. The scope of the invention will be measured by the appended claims and their equivalents.

The presen invention discloses methods and compositions for enhanced iontophoretic delivery of active agents.

Embodiments of the invention include pharmaceutically acceptable compositions for iontophoretic delivery comprising a delivery enhancing amount of vasodilator and active agent.

In addition, embodiments of the invention provide methods for enhancing iontophoretic delivery of active agents comprising:

(a) adding a delivery enhancing amount of a vasodilator to an active agent; and
(b) delivering of a pharmaceutically acceptable composition of (a) by iontophoresis.

The methods and compositions of the present invention are particularly advantageous compared to prior methods and compositions. Prior methods and compositions typically relied on skin damaging or skin altering compositions such as permeation enhancers. Unlike skin permeation enhancers that alter the stratum corneum, the compositions and methods of the present invention are not directed toward altering the stratum corneum and yet achieve an increase in active agent delivery. Likewise, the benefits obtained by the addition of a vasodilator to an active agent is opposite the generally held belief that lower concentration of other ions enhances delivery.

The following terms are defined as used in this document. "Ion" refers to an atom or radical that has lost or gained one or more electrons to acquire an electric charge. "Active agent" refers to the entity chosen to be delivered by iontophoresis. Thus, active agent refers to the chosen entity and the ionic form of the chosen entity for delivery, such as halide salts of a chosen entity to be delivered (e.g., lidocaine and an ionic form of lidocaine for delivery such as lidocaine hydrochloride). "Patient" refers to animals, including humans, household animals such as dogs and cats, livestock such as cattle, horses, sheep, pigs, goats and rabbits, laboratory animals such as mice and rats, and zoo animals such as exotic species.

The methods and compositions of the invention are not limited to practice with any one particular iontophoretic system. Generally, iontophoretic devices comprise at least two electrodes, an electrical energy source (e.g., a battery) and at least one reservoir which contains an active agent to be delivered. Several iontophoretic devices are known, such as those disclosed in P. Tyle, *Pharmaceutical Biosearch* 3:318 (1986).

Key components of the skin, as shown in FIG. 1, are the stratum corneum, epidermis, dermis and more specifically, the blood vessels of the dermis. In systemic drug delivery, the objective is to get the drug from a donor reservoir adjacent to the stratum corneum into the blood stream. In topical drug delivery, the objective is to get the drug from the donor reservoir adjacent to the stratum corneum into the skin below the stratum corneum while avoiding removal by the blood stream. Therefore, the structure of both the stratum corneum and the vascular is important.

When iontophoresis of an active agent is performed, the compound passes through the stratum corneum, through the intervening dermal tissue and into the vasculature. In a situation wherein the stratum corneum is the rate-limiting barrier, the blood flow in the vasculature is of little consequence. When the rate of delivery of the active agent is enhanced over passive delivery, as in the case of iontophoresis, to the point where the ability of the vasculature to remove the compound is rate limiting, then the blood flow in the vasculature becomes significant. Iontophoresis of a vasodilator with an active agent, therefore, is believed to enhance blood flow, thus enhancing the rate at which active agent is removed by the vasculature.

The ability to maintain proper concentration ratios of active agent to vasodilator will depend upon the iontophoretic properties of the active agent and vasodilator, and hence the relative proportions of the vasodilator combined with the active agent.

It is understood that most active agents have more than one effect in the body. For example, lidocaine is a local anesthetic which also exhibits vasoactive properties (i.e. a vasolidator). Therefore, consideration of these factors for any active agent must be taken into account when determining optimum ranges of each for iontophoretic delivery together.

The response surface method (RSM) is a known method that can be used to study the effects of active agent properties and vasodilator properties. Other methods for measuring the effects of the active agent and vasodilator are known. Other methods can be found in Chapter II of P. D. Halland, Experimental Design In Biotechnology (Marcell Dekker Inc., (1989) N.Y.).

Figure 4:
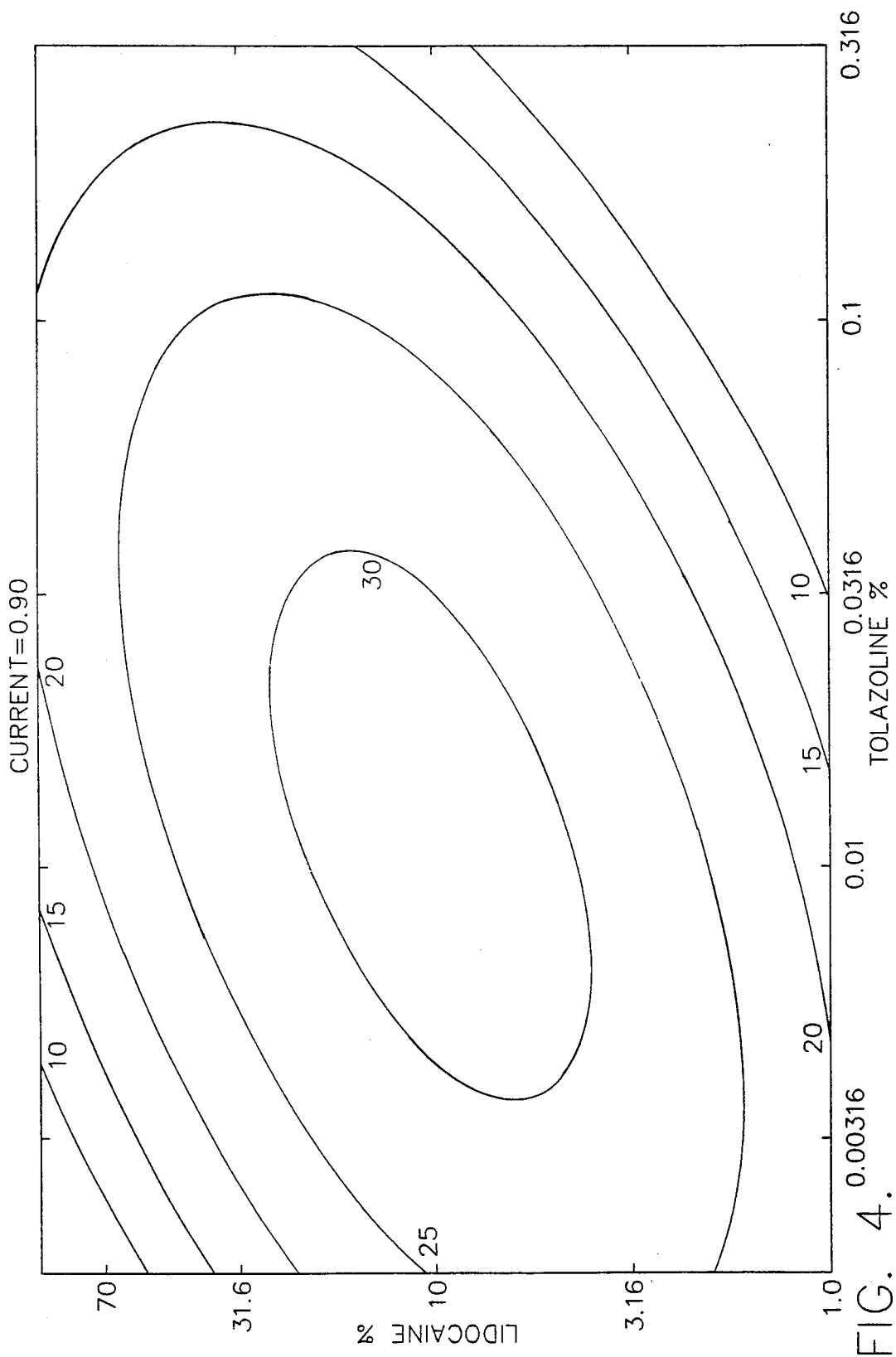
FIG. 4 is a contour plot showing delivery of an active agent when iontophoresed with a vasodilator.

The response surface method was used to determine the optimum concentrations of a composition of the active agent lidocaine and the vasodilator tolazoline. The results are easily determined as set forth in FIG. 4 and Example 1. A composition for enhanced iontophoretic delivery which comprises lidocaine as an active agent and tolazoline as a vasodilator preferable contains lidocaine in an amount of about 2.0% to about 60.0% in solvent and tolazoline in the amount of about 0.001% to about 0.1% in solvent. A more preferred composition for enhanced iontophoretic delivery of a composition which comprises lidocaine and tolazoline contains lidocaine in an amount of about 4.0% to about 25.0% in solvent and tolazoline in an amount of about 0.005% to about 0.05% in solvent. Optimum concentrations of other active agents and vasodilators are readily obtained in substantially the same manner.

The concentration or amount of vasodilator to active agent in a formulation or mixture is a function of the particular active agent and the vasodilator. More specifically, the ease with which the active agent may be delivered by iontophoresis is related to the characteristics of the vasodilator, the active agent, and to some extent the iontophoretic system.

Figure 2:
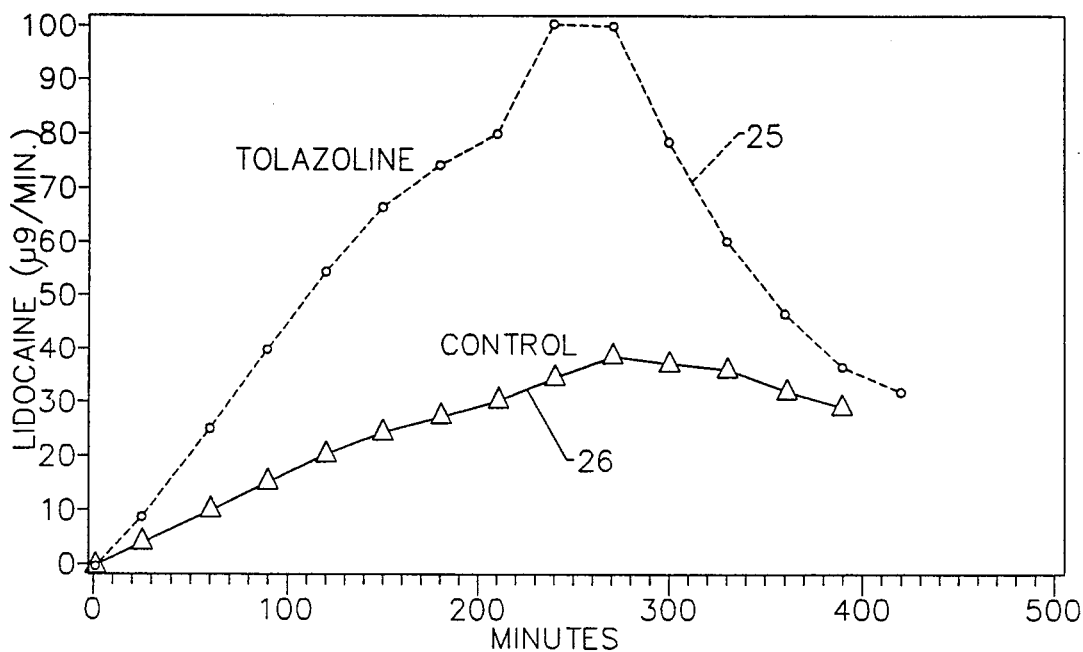
FIG. 2 is a plot of data showing that addition of the vasodilator tolazoline to a concentration of lidocaine enhances the iontophoretic rate of delivery of lidocaine.

The data shown in FIG. 2, for the vasodilator tolazoline and the active agent lidocaine, demonstrates the properties of a preferred composition of the invention. FIG. 2, in the upper plot, 25, shows the increase in the delivery of lidocaine with the addition of an optimum amount of the vasodilator tolazoline. Lower plot, 26, FIG. 2, shows iontophoresis of a control (−) without a vasodilator. The improvement in transdermal delivery by the iontophoresis of the active agent, lidocaine, with a vasodilator, is easily discernable by comparing plots 25 and 26. Iontophoretic administration rates are readily measured by protocols such as those disclosed in J. E. Riviere et al., *J. Toxicol—Cut. & Ocular Toxicol* 8:493 (1990)

Figure 3:
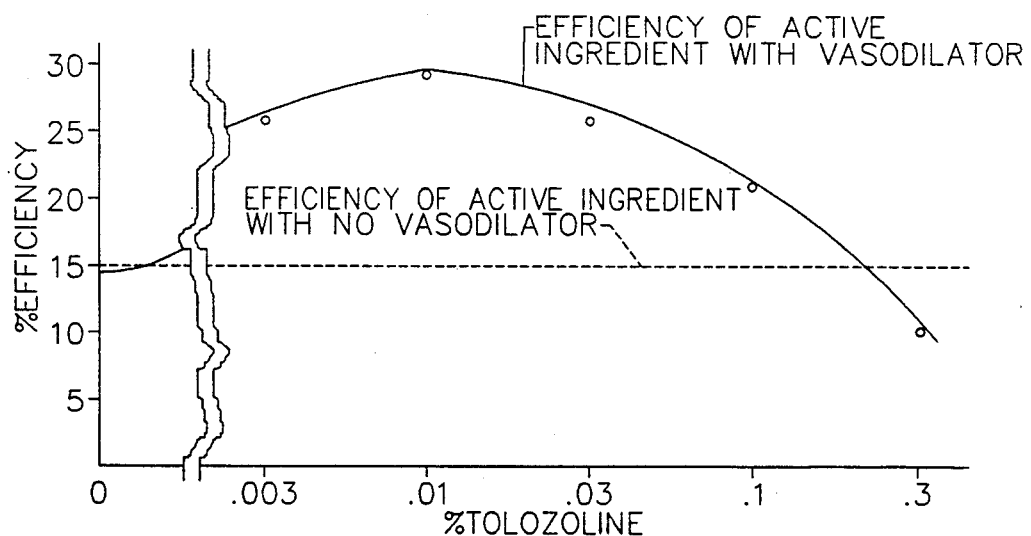
FIG. 3 is a plot of data showing the concentration of a vasodilator wherein delivery of the active agent is enhanced.

FIG. 3 shows that there is an optimum concentration of vasodilator when the concentration of the active agent is kept constant. With no vasodilator, the efficiency (e.i. same delivery with lower power) is on the order of 15%. At the optimum, the efficiency is over 30%. As more vasodilator is added, beyond the optimum concentration, the efficiency falls to a level lower than the original level.

A range of useful concentrations of the vasodilator with respect to the active agent is determined by analyzing the amount of active agent iontophoresed. Quantitation of active agent iontophoresed is obtained by following the procedure set forth in Example 2.

The concentration of the vasodilator will effect enhanced delivery of an active agent in two ways. When there is too much vasodilator, it is believed there is a change of blood flow at the deeper blood vessels of the skin, thus opening shunt blood vessels which will divert blood flow from the upper capillary loops, and therefore prevent enhancement of active agent delivery. The other effect is the result of the introduction of additional ions that compete with the ions of the active ingredient during coiontophoresis. The present invention provides a method for determining the optimimum concentration of vasodilator and active agent, which method accounts for competing ions in an iontophoretic system.

The present invention provides a method for obtaining optimum concentration at which enhancement of delivery is maximized. Iontophoresis of a composition of vasodilator and active agent is more efficient than iontophoresing active agent without a vasodilator. The addition of vasodilator permits the same delivery with a lower power.

The term "active agent" can more narrowly refer to a biologically active compound or mixture of compounds that have a therapeutic, prophylactic pharmacological, physiological, or combinations thereof, effect on the recipient and is sufficiently potent such that it can be delivered through the skin or other membrane to the recipient in sufficient quantities to produce the desired result.

The active agent for use in the method of the invention can be delivered alone, as a prodrug, or in combination with other substances. Other substances can include other permeation enhancers, buffers, bacteriostatics, stabilizers, antioxidants, other active agents and the like.

In general, active agents include therapeutic agents, or combinations thereof, in all of the major therapeutic areas including, but not limited to, anorexics, anthelmintics, antiasthma agents, anticonvulsants, antidiarrheals, antimigraine preparations, antimotion sickness, antinauseants, antieoplastics, antiparkinsonism drugs, antipruritics, antipyretics, anticholinergics, sympathomimetics, xanthine derivatives, cardiovascular preparations including calcium channel blockers, beta blockers, antiarrhythmics, antihypertensives, diuretics, vasodilators including general, coronary, peripheral and cerebral central nervous system stimulants, cough and cold preparations, decongestants, diagnostics, hormones, hypnotics, immunosuppressives, muscle relaxants, parasympatholytics, parasympathomimetics, psychostimulants, sedatives and tranguilizers, antiinflammatory agents, analgesics, antiarthritic agents, antispasmodics, antidepressants, antipsychotic agents, tranquilizers, antianxiety agents, narcotic antagonists, cholinergic agonists, anticancer agents, antiviral agents, antibiotic agents, appetite suppressants, antiemetics, anticholinergics antihistamines, antimigraine agents, contraceptive agents, antithrombotic agents, diuretics, antihypertensive agents, cardiovascular drugs and the like. Examples of specific drugs are steroids such as estradiol, progesterone, norgestrel, levonogestrel, norethindrone, medroxyprogestrone aceate, testosterone and their esters, nitro compounds such as nitroglycerine and isosorbide nitrates, nicotine, chlorpheniramine, terfenadine, triprolidine, hydrocortisone, oxicam derivatives such as piroxicam, ketoprofen, mucopolysaccharidases such as thiomucase, buprenorphine, fentanyl, naloxone, codeine, lidocaine, dihydroergotamine, pizotiline, salbutamol, terbutaline, prostaglandins such as misoprostol and enprostil, omeprazole, imipramine, benzamides such as metoclopramine, scopolamine, peptides such as growth releasing factor and somatostatin, clonidine, dihydropyridines such as nifedipine, verapamil, ephedrine, pindolol, metoprolol, spironolactone, nicardipine hydrochloride, calcitriol, thiazides such as hydrochlorothiazide, flunarizine, sydononimines such as molsidomine, sulfated polysaccharides such as heparin fractions proteins and peptides such as insulin and analogs thereof, calcitonin and analogs thereof such as elcatonin, protamine, glucagon, globulins, angiotensin I, angiotensin II, angiotensin III, lypressin, vasopressin, somatostatin and its analogs, growth hormones, and oxytocin, and the salts of such compounds with pharmaceutically acceptable acids or bases, as may be required. Preferably the active agent is a therapeutic anesthetic, hormone, protein, analgesic, or other low molecular weight cations. More preferably the active agent is lidocaine, insulin, calcitonin, elcatonin or somatostatin.

Primary requirements of an active agent are that it be charged or capable of modification to carry a charge. Appropriate selection of active agents for iontophoretic applications include selection based on specific conductivity (i.e., estimates how easily drugs move in solution when an electric current is applied).

Active agent modification for iontophoretic delivery is guided by well-known procedures. For example, to deliver a positively charged drug, the chloride or hydrochloride form of the drug can be made and placed in the iontophoretic device reservoir for delivery. General texts in the field include *Remington's Pharmaceutical Sciences*, Ed. Arthur Osol, 16th ed., 1980, Mack Publishing Co., Easton, Pa. Typically the basic ($OH^-$ or amine) or acid ($H^+$) form of the active agent is made, depending on whether the anionic (negative charged ion) or cationic (positive charged ion) form of the active agent is to be delivered. Common modifications of active agents include modification to a halide salt form. For example, to deliver a positively charged active agent, the chloride or hydrochloride form of the active agent is made and placed in the iontophoretic device reservoir for delivery. Likewise, the composition is typically dissolved in a suitable solvent to obtain the ionic form for iontophoretic delivery. Suitable solvents include polar liquids such as water, glycerine, and lower alkyl alcohols such as methyl alcohol, ethyl alcohol, and branched alcohols such as isopropyl alcohol.

In this invention the effective amount of active agent means that amount needed to produce the intended result following its iontophoretic administration. The effective amount will vary, depending, among other factors, on the physiological effect as determined by the serum level of desired active agent, rate of clearance of active agent, and intradermal metabolism desired.

The term pharmaceutically acceptable composition refers to the addition salts, mild complexes, solid and liquid carriers, ionic forms, and the like, which do not significantly or adversely affect the properties of the active agent or its ability to be iontophoretically delivered. Pharmaceutically acceptable compositions can be prepared by reference to general texts in the field, such as *Remington's Pharmaceutical Sciences*, Ed. Arthur Osol, 16th ed., 1980, Mack Publishing Co., Easton, Pa.

Delivery enhancing amount refers to an amount which enhances delivery of the active agent as compared to the active agent delivered alone, but which amount does not present serious side effects which outweigh the advantages of its use.

The reservoir or similar structure that contains the active agent to be delivered can be in the form of any material suitable for making contact between the iontophoresis unit and the skin. Suitable materials include, but are not limited to, foams, ion exchange resins, gels and matrices.

Iontophoresis gels can be karaya gum, other polysaccharide gels, or similar hydrophilic aqueous gels capable of carrying ions. Specific examples of such gels include polyvinyl alcohol, polymethyl pyrollidine, methyl cellulose, polyacrylamide, polyhemas, polyhema derivatives and the like. The matrix selected should have nonirritating properties to avoid irritating the person's skin or tissue, suitable viscosity and surfactant properties to obtain good electrical contact with the skin or tissue, and the ability to act as a carrier medium for the ions.

Suitable vasodilators for use in the present invention can be selected from the major categories of vasodilators generally referred to as cerebral, coronary and peripheral. Specific vasodilators within the cerebral category include bencyclane, cinnarizine, citicoline, cyclandelate, ciclonicate, diisopropylamine dichloroacetate, eburnamonine, fenoxedil, flunarizine, ibudilast, ifenprodil, nafronyl, nicametate, nicergoline, nimodipine, papaverine and penifylline.

Specific vasodilators within the coronary category include amotriphene, bendazol, benfurodil hemisuccinate, benziodarone, chloracizine, chromonar, clobenfurol, clonitrate, dilazep, dipyridamole, droprenilamine, efloxate, erythritol, erythrityl tetranitrate, etafenone, fendiline, floredil, ganglefene, hexestrol bis(B-diethylaminoethyl ether), hexobendine, itramin tosylate, khellin, lidoflazine, mannitol hexanitrate, medibazine, nicorandil, nitroglycerin, pentaerythritol tetranitrate, pentrinitrol, perhexiline, pimefylline, prenylamine, propatyl nitrate, pyridofyline, trapidil, tricromyl, trimetazidine, trolnitrate phosphate, and visnadine.

Specific vasodilators within the peripheral category include aluminum nicotinate, bamethan, bencyclane, betahistine, bradykinin, brovincamine, bufeniode, buflomedil, butalamine, cetiedil, ciclonicate, cinepazide, cinnarizine, cyclandelate, diisopropylamine dichloroacetate, eledoisin, isoxsuprine. kallidin, kallikrein, moxisylyte, nafronyl, nicametate, nicergoline, nicofuranose, nicotinyl alcohol, nylidrin, pentifylline, pentoxifylline, piribedil, prostaglandin $E_1$, suloctidil, tolazoline, and xanthinol niacinate. Preferably the vasodilators are selected from the peripheral category.

All of the compounds are readily described in The Merck Index, Eleventh Edition (Merck and Co., Inc., Rahway, N.J. (1989)).

The treatment regimen for use in the present invention includes the consideration of a variety of factors, including the type, age, weight, sex, medical condition of the patient, severity of the condition and active agent to be delivered. An ordinarily skilled physician can readily determine and prescribe and administer the effective amount of the agent required to prevent or arrest the progress of the condition. In so proceeding, the physician could employ relatively low doses at first and subsequently increase the dose until a maximum response is obtained. Likewise, the decision of where to apply the iontophoretic system is a factor, depending on the area of application, for example, whether the area is on the torso or the extremities and whether those areas are hairy, wrinkled, folded or creased.

The following examples illustrate the specific embodiments of the invention described herein. As would be apparent to skilled artisans, various changes and modifications are possible and are contemplated within the scope of the invention described.

EXAMPLES

Material Preparation

The electrodes used herein have a surface area about 10 $cm^2$ (2.5cm $\times$ 4 cm) and are fabricated as a sandwich. The outer layers of the sandwich consist of about 1/16 inch POREX TM (a thick porous, hydrophilic open-cell polyethylene foam into which a surfactant has been incorporated during manufacture, obtainable from Porex Technologies, Fairburn, Ga.). The inner layer of the sandwich electrode consists of about 1.5 cm $\times$ 5 cm mesh of silver wire (0.0045 inch silver wire 80 $\times$ 80 weave, obtainable from Unique Wire Weaving Co., Hillside, N.J.). About 1.5 cm $\times$ 1 cm tab of silver mesh is left protruding from the polyethylene sandwich for purposes of making electrical contact. The sandwich is held together by an epoxy type glue (e.g., DEVCON TM 5-minute epoxy glue, obtainable from Devcon Corp., St. Louis, Mo.) along the lateral edges of the polyethylene.

Using scissors, two rectangular pieces are cut from the 1/16 inch thick sheet of POREX TM material. Each piece is about 2.5cm $\times$ 4cm. A 1 cm $\times$ 5 cm piece of the silver wire mesh is then cut. The mesh is longitudinally centered on one piece of the POREX TM, with about 1 cm of material extending out one end. A line of epoxy type glue is placed along the inner border of lateral edges and the end of the POREX TM. Take care not to place the glue on the wire mesh itself. It is both understood and desirable that the applied glue will contact the edges of the wire mesh and, by so doing, hold the mesh securely in position. However, the amount of that contact should be kept at a minimum.

Sandwich the wire mesh by placing the second piece of POREX TM over the first. Place the completed unit in the clamp and allow to dry about 40 minues. Examine the electrode to see that all three glued edges are in tight contact. Test the integrity of the mesh Porex TM attachment by gently tugging on the protruding edge of mesh. The mesh should not shift in position. Stre in a dry area.

EXAMPLE 1

The following protocol is referred to as the Response Surface Method (RSM). Drug formulation for each experiment is shown in the summary below for the active (positive) electrode. Drug formulation for the indifferent (negative) electrode is unbuffered normal saline.

Standard methods for flap surgery and preparation are used herein. Standard methods for flap perfusion and maintenance are used; non-recirculating perfusate is used without exception. Standard flap surgery and methods for flap perfusion are known by reference to publications such as Monteiro Riviere, N.A., et al., The Isolated Perfused Porcine Skin Flap (IPPS) "II Ultra Structural and Histological Characterization of Epidermal Viability", *In Vitro Toxicology*, 1:241 (1987). A volume of venous exudent is collected, at least 1.0 ML but not exceeding 3.0 ML at one half hour increments after iontophoresis begins. For control purposes, two venous effluent specimens are collected prior to iontophoresis. A total of 18 venous effluent specimens are collected in total, two before iontophoresis, and 16 covering 4 hours of iontophoresis and 4 hours past iontophoresis.

Voltage measurements are also taken by measuring output of the constant current generator, for example, WPI Model A360, available from World Precision instruments, New Haven, Conn.

All venous effluent specimens are analyzed for lidocaine using the standard lidocaine assay procedure described in the following example. Mixing instructions for the active electrode formulations are listed below:

To Prepare

---

3.16% lidocaine, add 36.5 mgm lidocaine HCL/ML H$_2$O
31.6% lidocaine, add 36.5 mgm lidocaine HCL/ML H$_2$O
10% lidocaine, add 115.6 mgm lidocaine HCL/ML H$_2$O
1.45% lidocaine, add 16.8 mgm lidocaine HCL/ML H$_2$O
70% lidocaine, add 809 mgm lidocaine HCL/ML H$_2$O
0.01% tolazoline, add 122.8 mgm tolazoline HCL/ML H$_2$O
0.1% tolazoline, add 1.228 mgm tolazoline HCL/ML H$_2$O
0.0316% tolazoline, add 388 mgm tolazoline HCL/ML H$_2$O
0.0045% tolazoline, add 55.3 mgm tolazoline HCL/ML H$_2$O
0.215% tolazoline, add 2.640 mgm tolazoline HCL/ML H$_2$O
FW lidocaine = 234.22
FW lidocaine HCL = 270.68
FW tolazoline = 160.21
FW tolazoline HCL = 196.67
Before starting, test mix: 70% lidocaine and .0316% totazoline to insure it goes into solution.
Protocol
non recirculating perfusate
4 hours iontophoresis
8 hours sampling, sample every ½ hour

---

Before starting, test mix: 70% lidocaine and 0.0316% tolazoline to insure it goes into solution. Protocol—non-recirculating perfusate 4hours iontophoresis 8 hours sampling, sample every ½ hour

| RUN | CURRENT*ma | % LIDOCAINE (W/V) | % TOLAZOLINE (W/V) |
|---|---|---|---|
| 1 | 1.35 | 3.16 | 0.01 |
| 2 | 1.35 | 31.6 | 0.10 |
| 3 | 0.90 | 10.0 | 0.0316 |
| 4 | 0.45 | 31.6 | 0.01 |
| 5 | 0.45 | 3.16 | 0.10 |
| 6 | 0.45 | 3.16 | 0.01 |
| 7 | 0.45 | 31.6 | 0.10 |
| 8 | 1.35 | 3.16 | 0.10 |
| 9 | 0.90 | 10.0 | 0.0316 |
| 10 | 1.35 | 31.6 | 0.01 |
| 11 | 0.90 | 1.45 | 0.0316 |
| 12 | 0.90 | 70.0 | 0.0316 |
| 13 | 0.90 | 10.0 | 0.0045 |
| 14 | 0.90 | 10.0 | 0.0316 |
| 15 | 0.90 | 10.0 | 0.215 |
| 16 | 1.65 | 10.0 | 0.0316 |
| 17 | 0.90 | 10.0 | 0.0316 |
| 18 | 0.15 | 10.0 | 0.0316 |
| 19 | 0.90 | 10.0 | 0.215 |
| 20 | 0.90 | 10.0 | 0.0045 |
| 21 | 1.65 | 10.0 | 0.0316 |
| 22 | 0.15 | 10.0 | 0.0316 |
| 23 | 0.90 | 1.45 | 0.0316 |
| 24 | 0.90 | 70.0 | 0.0316 |

*based on an electrode area of 4.5 cm$^2$, and current densities of 100 μA/cm$^2$, 200 μA/cm$^2$, and 300 μA/cm$^2$

EXAMPLE 2

Quantitation of lidocaine concentrations in samples generated by perfused skin flap iontophoresis experiments is performed as follows:

Equipment

1. Hewlett-Packard (Palo Alto, Calif.) 5840a gas chromatograph (GC), or equivalent, with flame ionization detector(FID), auto liquid sampler, J. and W. Scientific (Follsom, CA) "megabore" column, Cat. No. 125-1012, DB-1+, 15 m long, 1.5 micron film thickness; or equivalent, with appropriate injector and detector connections.
2. Vortex mixer.
3. Beckman Microfuge B, or equivalent.
4. Pipettes for quantitative transfer of 50-250 microliter volumes.
5. Crimper for 12 mm crimp-seal vial caps.

Consumables

1. Microfuge tubes with snap-caps; 1.5 ml, polypropylene.
2. Ammonium hydroxide, 1.5 M.
3. Solvent mixture: 2%(v/v) 2 - propanol in N-heptane.
4. Autosampler vials (12×32mm) and crimp seal (teflon-lined rubber septa) caps.
5. Autosampler vial inserts.
6. Pasteur Pipettes.
7. Lidocaine hydrochloride (minimum purity 99%).
8. Plastic (PS) 15 ml centrifuge tubes (Falcon #2095, obtainable from Falcon Products, Becton Dickinson Labware, Oxnard, Calif.), or equivalent.
9. Transfer pipette tips.

Generally 1.0 ml samples are taken of the venus effluent (perfusate) of the skin flap. The minimum lidocaine level which can be determined by this method is about 10 microgram/ml, in the perfusate. This minimum could easily be decreased, if desired, by using a larger GC injection volume than is indicated. Once step C, below, is completed, the remaining portions of the extraction, transfer of the organic extract to an autosampler vial and sealing of the vial should be completed as soon as possible to avoid errors due to evaporation of the organic solvent. If the extracted samples are not to be analyzed immediately, they should be stored in a freezer.

Extraction from the aqueous solution is as follows:
a. 200 microliter of the sample solution containing the lidocaine is accurately transferred to a 1.5 ml polypropylene microfuge tube with snap cap.
b. 50 microliter of 1.5 N NH$_4$OH is added to the tube.
c. 250 microliter of 2% isopropyl alcohol in normal heptane is added and the tube is capped.
d. The contents are gently swirled utilizing a vortex mixer for 1 minute.
e. Separate the organic and aqueous fractions by centrifugation employing a microfuge (about 5-10 minutes).
f. Place a 100 microliter insert in each GC Autosampler vial.
g. Using a Pasteur pipette transfer the upper organic fraction from the microfuge tube to a GC autosampler vial (it must be at least half full) and seal the vial with a crimp seal cap.

A stock solution of lidocaine HCl is prepared which contains 1.0 mg/ml lidocaine as free base (f.b.) by dissolving 577.9 mg of the hydrochloride salt in 500 ml deionized water. Quantitative measures are required.

---

Molecular Weights
lidocaine free base = 234.3
lidocaine-HCl = 270.8
500 mg lidocaine f.b. = (270.8/234.3) * 500
500 mg lidocaine f.b. = 577/9 mg lidocaine-HCl A series of 10 ml standard dilutions which cover the range of sample concentrations is prepared by dilution of the stock with the matrix solution. The required volume of stock is transferred with a pipette to a volumetric flask which is filled to the mark and mixed well.

Two sets of extracted standards are prepared from the standard dilutions by using the same extraction procedure described above for the unknown sample solutions.

The following program for GC set-up is used with normal (FID) detection and an injection volume of 1 microliter.

| | |
|---|---|
| TEMP 1: | 170 |
| TIME 1: | 10 |
| INJ TEMP | 250 |
| FID TEMP | 300 |
| AUX TEMP | (This does not matter) |
| CHT SPD | 0.50 |
| ZERO | 10.0 |
| ATTN 2 | 7 |
| FID SIG | A |
| SLOPE SENSE | 1 |
| AREA REJ | 0 |
| FLOW A | 30 |
| FLOW B | (This does not matter) |

A calibration plot is constructed by plotting the area counts for the calibration standards (on the "Y" axis) against the concentrations of lidocaine in the standard dilutions (on the "X" axis). A linear regression analysis on the data gives the best straight line fit. The equation for the straight line is used to determine the concentrations in the samples from their lidocaine peak area counts. The regression analysis and plotting are conveniently done with the Statgraphics PC program available from STSC, Inc., Rockville, Md.

EXAMPLE 3

A method similar to that described above was developed to analyze lower concentration samples (such as found in perfused skin flap experiments). However, a larger sample volume is required (0.5 ml). This method gives a detection limit of about 2 microgram/ml. Procedures outlined in the method above are followed except for the changes indicated below:

1. Pipet 0.5 ml of sample into a 1.5 ml microfuge tube.
2. Add 0.20 ml 1.5 N NH$_4$OH and 0.20 ml of organic solvent mixture (2-propanol/heptane).
3. Vortex mix, centrifuge and transfer as described above.
4. Set the GC injection volume to 3 microliters.

Although the invention has been described with respect to specific modifications, the details thereof are not to be construed as limitations, for it will be apparent that various equivalents, changes and modifications may be resorted to without departing from the spirit and scope thereof and it is understood that such equivalent embodiments are to be included therein.

What is claimed is:

1. A method for enhancing iontophoretic delivery of an active agent comprising:
    (a) providing an iontophoretic delivery system comprising a reservoir and an electrical energy source, said reservoir containing a pharmaceutically acceptable composition comprising an active agent and a delivery enhancing amount of a vasodilator;
    (b) contacting said iontophoretic delivery system to the skin of a subject; and
    (c) delivering said pharmaceutically acceptable composition to the subject by iontophoresis;
    wherein said delivery enhancing amount of vasodilator is from about 0.001% to about 0.1% in solvent.
2. The method of claim 1 in which the vasodilator is selected from the group consisting of cerebral vasodilators, coronary vasodilators, and peripheral vasodilators.
3. The method of claim 2 in which the vasodilator is a cerebral vasodilator.
4. The method of claim 2 in which the vasodilator is a coronary vasodilator.
5. The method of claim 2 in which the vasodilator is a peripheral vasodilator.
6. The method of claim 3 in which the active agent is selected from the group consisting of therapeutics, anesthetics, hormones and proteins.
7. The method of claim 6 in which the active agent is an anesthetic.
8. The method of claim 1 in which the delivery enhancing amount of vasodilator is from about 0.005% to about 0.05% in solvent.
9. The method of claim 1 in which the active agent is lidocaine and the vasodilator is tolazoline.
10. The method of claim 9 in which the lidocaine is from about 2.0% to 60.0% in solvent and the tolazoline is from about 0.001% to 0.1% in solvent.
11. The method of claim 10 in which the lidocaine is from about 4.0% to 25.0% in solvent and the tolazoline is from about 0.005% to 0.05% in solvent.

* * * * *